United States Patent
Kimmich et al.

(10) Patent No.: US 8,076,506 B2
(45) Date of Patent: Dec. 13, 2011

(54) PROCESS FOR THE REDUCTION OF ALDEHYDE CONCENTRATION IN A TARGET STREAM

(75) Inventors: Barbara F. M. Kimmich, League City, TX (US); Jeremy J. Patt, League City, TX (US); Mark O. Scates, Houston, TX (US); Ronald D. Shaver, Houston, TX (US); James H. Zink, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 461 days.

(21) Appl. No.: 12/226,096

(22) PCT Filed: Apr. 3, 2007

(86) PCT No.: PCT/US2007/008406
§ 371 (c)(1),
(2), (4) Date: Oct. 7, 2008

(87) PCT Pub. No.: WO2007/120554
PCT Pub. Date: Oct. 25, 2007

(65) Prior Publication Data
US 2010/0204512 A1     Aug. 12, 2010

Related U.S. Application Data

(60) Provisional application No. 60/792,244, filed on Apr. 14, 2006.

(51) Int. Cl.
C07C 51/10 (2006.01)
C07C 51/12 (2006.01)
(52) U.S. Cl. .......................... 562/517; 562/518; 562/519
(58) Field of Classification Search .................. None
See application file for complete search history.

(56) References Cited

U.S. PATENT DOCUMENTS

| | | | | |
|---|---|---|---|---|
| 5,155,266 A | * | 10/1992 | Scates et al. | 562/608 |
| 2002/0151746 A1 | * | 10/2002 | Scates et al. | 562/519 |

* cited by examiner

*Primary Examiner* — Paul A Zucker

(57) ABSTRACT

A process for reducing the aldehyde concentration in a target stream of a carbonylation process is disclosed. More specifically, a process for reducing the aldehyde concentration in an internal process stream or feed stream of a carbonylation process is disclosed. In particular, a process in which a target stream comprising a carbonylatable reactant and a first aldehyde concentration is subjected to a reaction comprising a supported catalyst that comprises at least one Group 8 to Group 11 metal at conditions sufficient to reduce the first aldehyde concentration to a second aldehyde concentration is disclosed.

46 Claims, No Drawings

PROCESS FOR THE REDUCTION OF ALDEHYDE CONCENTRATION IN A TARGET STREAM

This application claims benefit of 60/792,244 filed Apr. 14, 2006.

BACKGROUND OF THE INVENTION

1. Field of the Invention

This invention relates to a process for reducing the aldehyde concentration in a target stream. The invention, in particular, relates to a process for reducing the aldehyde concentration in a target stream of a carbonylation process. The invention also relates to a process for reducing the aldehyde concentration in a target stream comprising a carbonylatable reactant. More particularly, this invention relates to a process for reducing the aldehyde concentration in a feed stream to a carbonylation reactor of a carbonylation process.

2. Technical Background

Among currently employed processes for synthesizing acetic acid, one of the most useful commercially is the catalyzed carbonylation of a carbonylatable reactant(s), in particular methanol, with carbon monoxide as taught in U.S. Pat. No. 3,769,329, issued to Paulik et al. on Oct. 30, 1973. The carbonylation catalyst typically contains rhodium, either dissolved or otherwise dispersed in a liquid reaction medium or supported on an inert solid, along with a halogen-containing catalyst promoter as exemplified by methyl iodide. The rhodium can be introduced into the reaction system in any of many forms. Likewise, the nature of the halide promoter is not generally critical. The patentees disclose a very large number of suitable promoters, most of which are organic iodides. Most typically and usefully, the reaction is conducted by continuously bubbling carbon monoxide gas through a liquid reaction medium in which the catalyst is dissolved.

An improvement in the prior art process for the carbonylation of an alcohol to produce the carboxylic acid having one carbon atom more than the alcohol in the presence of a rhodium catalyst is disclosed in commonly assigned U.S. Pat. No. 5,001,259, issued Mar. 19, 1991; U.S. Pat. No. 5,026,908, issued Jun. 25, 1991; and U.S. Pat. No. 5,144,068, issued Sep. 1, 1992; and European Patent No. EP 0 161 874 B2, published Jul. 1, 1992. As disclosed therein, acetic acid is produced from methanol in a reaction medium containing methyl acetate, methyl halide, especially methyl iodide, and rhodium present in a catalytically effective concentration. These patents disclose that catalyst stability and the productivity of the carbonylation reactor can be maintained at surprisingly high levels, even at very low water concentrations, i.e., 4 weight percent or less, in the reaction medium (despite the general industrial practice of maintaining approximately 14-15 wt % water) by maintaining in the reaction medium, along with a catalytically effective amount of rhodium and at least a finite concentration of water, a specified concentration of iodide ions over and above the iodide ion that is present as hydrogen iodide. This iodide ion is a simple salt, with lithium iodide being preferred. The patents teach that the concentration of methyl acetate and iodide salts are significant parameters in affecting the rate of carbonylation of methanol to produce acetic acid, especially at low reactor water concentrations. By using relatively high concentrations of the methyl acetate and iodide salt, one obtains a surprising degree of catalyst stability and reactor productivity even when the liquid reaction medium contains water in concentrations as low as about 0.1 wt %, so low that it can broadly be defined simply as "a finite concentration" of water. Furthermore, the reaction medium employed improves the stability of the rhodium catalyst, i.e., resistance to catalyst precipitation, especially during the product recovery steps of the process. In these steps, distillation for the purpose of recovering the acetic acid product tends to remove from the catalyst the carbon monoxide, which in the environment maintained in the reaction vessel, is a ligand with stabilizing effect on the rhodium. U.S. Pat. Nos. 5,001,259, 5,026,908 and 5,144,068 are herein incorporated by reference.

It has been found that although a low water carbonylation process for producing acetic acid reduces such by-products as carbon dioxide, hydrogen, and propionic acid, the amount of other impurities, present generally in trace amounts, can be increased by a low water carbonylation process, and the quality of acetic acid sometimes suffers when attempts are made to increase the production rate by improving catalysts, or modifying reaction conditions.

These trace impurities affect quality of acetic acid, especially when they are recirculated through the reaction process, which, among other things, can result in the build up over time of these impurities. Unsaturated aldehydes, notably crotonaldehyde and ethyl crotonaldehyde, which are derived from aldol reactions of acetaldehyde, are impurities that decrease the permanganate time of the acetic acid, a quality test commonly used in the acetic acid industry. As used herein, the phrase "aldehyde" is intended to mean compounds that contain aldehyde functional groups, which compounds may or may not possess unsaturation. See *Catalysis of Organic Reaction*, 75, 369-380 (1998), for further discussion on impurities in a carbonylation process. Such aldehyde species may be found in any number of streams of the carbonylation process. As disclosed, such aldehyde species can be generated within the process. As such, aldehyde species may be found within any number of internal process streams. Such aldehyde species are also often found in feed materials commonly used for the carbonylation process. Common industrial sources of carbonylatable reactants may contain aldehyde species, which may be present in undesirable concentrations. As such, aldehyde species may be found in a feed stream provided to the carbonylation reactor. Such streams, e.g., process and feed streams, of the carbonylation process will typically contain at least one carbonylatable reactant.

The present invention is directed to reducing aldehyde concentration, which may be present as compounds such as acetaldehyde, butyraldehyde, crotonaldehyde, 2-ethyl crotonaldehyde, and 2-ethyl butyraldehyde and the like, particularly in a target stream comprising a carbonylatable reactant or a target stream of a carbonylation process.

The aldehyde species described above, such as acetaldehyde, are sources for any number of other undesirable byproducts that may be formed in a carbonylation process. Acetaldehyde, in particular, is a source of propionic acid. By reducing the aldehyde concentration, the present invention may also lead to reduction or removal of such undesirable byproducts. Accordingly, it is a primary objective to reduce aldehyde species, notably acetaldehyde.

Conventional techniques to remove such aldehyde impurities include treating the acetic acid product streams with oxidizers, ozone, water, methanol, activated-carbon, amines, and the like. Such treatments may or may not be combined with distillation of the acetic acid. The most typical purification treatment involves a series of distillations of the final product. It is also known to remove aldehyde impurities from organic streams by treating the organic streams with an amine compound such as hydroxylamine, which reacts with the aldehyde species to form oximes, followed by distillation to separate the purified organic product from the oxime reaction products. However, the additional treatment of the final product adds cost to the process, and distillation of the treated acetic acid product can result in additional impurities being formed.

It has thus become important to identify more economically viable methods of reducing the concentration of aldehyde species within the carbonylation process, including process streams and feed streams containing a carbonylatable reactant, without contaminating the final product or adding unnecessary costs. Accordingly, there remains a need for alternative processes to improve the efficiency of aldehyde reduction. The present invention provides one such alternative solution.

SUMMARY OF THE INVENTION

This invention relates to a process for reducing the aldehyde concentration in a target stream. The invention, in particular, relates to a process for reducing the aldehyde concentration in a target stream of a carbonylation process. The invention also relates to a process for reducing the aldehyde concentration in a target stream comprising a carbonylatable reactant. More particularly, this invention relates to a process for reducing the aldehyde concentration in a feed stream to a carbonylation reactor of a carbonylation process.

In one aspect, the present invention provides a process comprising providing a target stream that comprises a carbonylatable reactant and a first aldehyde concentration; and subjecting the target stream to a reaction comprising a supported catalyst that comprises at least one Group 8 to Group 11 metal at conditions sufficient to reduce the first aldehyde concentration to a second aldehyde concentration.

In another aspect, the present invention provides a process comprising providing a target stream of a carbonylation process comprising a first aldehyde concentration; providing the target stream to a reaction vessel containing a supported catalyst comprising at least one Group 8 to Group 11 metal; subjecting the target stream to conditions sufficient to reduce the first aldehyde concentration; and removing from the reaction vessel a treated stream comprising a second aldehyde concentration that is less than the first aldehyde concentration.

In another aspect, the present invention provides a process comprising providing a feed stream of a carbonylation process comprising a carbonylatable reactant and a first aldehyde concentration; providing the feed stream to a reaction vessel containing a supported catalyst comprising at least one Group 8 to Group 11 metal; subjecting the feed stream to conditions sufficient to reduce the first aldehyde concentration; and removing from the reaction vessel a treated stream comprising a second aldehyde concentration that is less than the first aldehyde concentration.

While the invention is susceptible to various modifications and alternative forms, specific embodiments have been shown by way of example and will be described in detail herein. It should be understood, however, that the invention is not intended to be limited to the particular forms disclosed. Rather, the invention is intended to cover all modifications, equivalents, and alternatives falling within the scope of the invention as defined by the appended claims.

DESCRIPTION OF ILLUSTRATIVE EMBODIMENTS

This invention relates to a process for reducing the aldehyde concentration in a target stream. The invention, in particular, relates to a process for reducing the aldehyde concentration in a target stream of a carbonylation process. The invention also relates to a process for reducing the aldehyde concentration in a target stream comprising a carbonylatable reactant. More particularly, this invention relates to a process for reducing the aldehyde concentration in a feed stream to a carbonylation reactor of a carbonylation process.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

In the various embodiments of the present invention, a process is provided for reducing the aldehyde concentration in a target stream that comprises at least one aldehyde species in a first aldehyde concentration. In certain embodiments, a target stream of a carbonylation process, which may or may not contain a carbonylatable reactant, is employed. In certain embodiments, a process is provided for reducing the aldehyde concentration in a feed stream of a carbonylation process that comprises at least one carbonylatable reactant and at least one aldehyde species in a first aldehyde concentration.

In the various embodiments, the target stream comprising a first aldehyde concentration is subjected to a reaction comprising contacting the target stream with a supported catalyst that comprises at least one Group 8 to Group 11 metal under conditions sufficient to reduce the first aldehyde concentration to a second aldehyde concentration. As a result of conducting the process, a desired reduction in the concentration of aldehyde species can be achieved and a treated stream containing the second aldehyde concentration can be separated. The treated stream can be advantageously used in subsequent processes or process steps where it is desirable to have reduced aldehyde concentration.

The invention is not generally limited by the concentration of aldehyde species comprising the first aldehyde concentration. Desirable process conditions for conducting the process may vary depending on the concentration of aldehyde species comprising the first aldehyde concentration in the target stream.

As previously disclosed, "aldehyde species" means a compound or compounds that contain aldehyde functional groups, which compounds may or may not possess unsaturation. Aldehyde species, whose concentration in a stream can be reduced by practicing the present invention, include acetaldehyde, butyraldehyde, crotonaldehyde, 2-ethyl crotonaldehyde, 2-ethyl butyraldehyde, and the like. A particularly desirable use of the present invention is to reduce the concentration of acetaldehyde.

The aldehyde species in the target stream is present at a first aldehyde concentration, which may be the concentration of a single aldehyde species if only a single aldehyde species is present in the target stream or the cumulative concentration of two or more aldehyde species, if more than one aldehyde species is present in the target stream. Similarly, the second aldehyde concentration, such as may be found in the treated stream, may be the concentration of a single aldehyde species if only a single aldehyde species is present or the cumulative concentration of two or more aldehyde species, if more than one aldehyde species is present. The reduction in aldehyde concentration may be due to the reduction in concentration of one or more individual aldehyde species.

Catalysts that can be used in accordance with the invention are supported catalysts that comprise at least one Group 8 to Group 11 metal. The nature of the supports that may be employed with the present invention is not generally limited and it is generally expected that those supports finding applicability in common commercial chemical processes can likely be used in accordance with the present invention. Acceptable supports include both organic and inorganic supports. Acceptable organic or carbon supports include, but are not limited to, supports based on coconut, bituminous carbon, charcoal, and other carbons. Acceptable inorganic supports include, but are not limited to, supports based on metal oxides, such as alumina, silica, titania, zirconia, and magnesia; mixed-metal oxides; clay; and silicon carbide. It may be desirable in certain embodiments that supports be low in sulfur content. Similarly, the physical properties of supports that can be used in practicing the present invention are not generally limited by properties commonly used to characterize supports, including, but not limited to, pore size, surface area, water absorption, and other properties.

As previously indicated, catalysts that can be used in accordance with the invention are supported catalysts that comprise at least one Group 8 to Group 11 metal. Preferably, the catalyst comprises at least one Group 8 to Group 10 metal. Even more preferably, the catalyst comprises at least one Group 10 metal. Preferred catalysts comprise ruthenium, palladium, and/or platinum, more preferably palladium and/or platinum, and even more preferably palladium. While the catalyst may comprise a single Group 8 to Group 11 metal, catalysts may be employed comprising more that one Group 8 to Group 11 metal.

The metal concentrations that can be used in practicing the present invention are not generally limited. Supported catalysts of various metals at various concentrations and on various supports that can be used in accordance with the present invention are generally available from various commercial sources. Desirable catalysts may contain greater than 0.01 weight percent metal, greater than 0.1 weight percent metal, greater than 0.25 weight percent metal, or even greater than 0.5 weight percent metal. Desirable catalysts may contain less than 5.0 weight percent metal, less than 2.5 weight percent metal, and even less than 1.0 weight percent metal.

Catalysts that have been used in conjunction with the present invention include commercial catalysts such as 0.5 wt. % Pd on granulated carbon (Engelhard Co., product no. C3880), 0.5 wt. % Pt on granulated carbon (Engelhard Co., product no. C3757), and 1.0 wt. % Ru on granulated carbon (Catalyst C, 5.5 g, Engelhard Co., product no. C4023).

While it is preferable that a single type of support be used with single catalytic metal or single combination of catalytic metals, the use of multiple types of supports and/or multiple catalytic metals is contemplated and not outside the scope of this invention. Preferred catalysts include those comprising palladium or platinum on a carbon support.

In the various embodiments of the present invention, the target stream is subjected to a reaction comprising contacting the target stream with a supported catalyst that comprises at least one Group 8 to Group 11 metal at conditions sufficient to reduce the first aldehyde concentration to a second aldehyde concentration. The conditions under which the process can be operated to obtain the desired result fall within two basic regimes: an oxidation regime and a decomposition regime. In the oxidation regime, the reaction is conducted in the presence of oxygen. The oxygen may be present as pure oxygen, air, or combinations of pure oxygen and air. Compounds that serve as an oxygen source can also be used. Preferably, the oxygen is provided as air. Under the oxidation regime, the reaction resulting in the reduction of aldehyde concentration can occur at any concentration of available oxygen, even a finite concentration of oxygen. Thus in addition to oxygen, an inert carrier, such as nitrogen, may be employed. One of ordinary skill in the art having the benefit of this disclosure will recognize that the process can be conducted at milder conditions, such as temperature and pressure, as higher oxygen concentrations are employed. It is possible to conduct the process under flammable conditions. Desirably, the oxygen concentration and the temperature are set and/or maintained in order to achieve the desired reduction of aldehyde. One skilled in the art will recognize that oxygen concentration and temperature can have an impact, even a significant impact, on the catalyst life and performance. The oxygen concentration and temperature are desirably chosen such that the conversion is at a desired level, and the lifetime of the catalyst is maximized while minimizing the destruction of carbonylatable reactants and other components that may be present and minimizing the formation of undesired byproducts.

When operating in the oxidation regime, the molar ratio of oxygen fed to the reaction, i.e., oxygen feed, to first aldehyde concentration is preferably greater than 0.1, more preferably greater than 0.5, more preferably greater than 1, even more preferably greater than 5, and even more preferably greater than 7.5. The maximum molar ratio of oxygen feed to first aldehyde concentration is not generally limited; however, it may be desirable in certain embodiments to limit the amount of oxygen feed based on a desire to stay under the flammability limit or to minimize formation of undesired byproduct.

In the decomposition regime, the process is conducted in the absence of oxygen. In the decomposition regime, the target stream can be diluted with an inert gas or gases. Alternatively, the target stream may be subjected to the process without the use of an inert carrier gas.

Under either an oxidation regime or a decomposition regime, the target stream is preferably provided to a vessel containing the catalyst under conditions, notably temperature and pressure, such that the target stream is in the gas phase, i.e., above the target stream's dew point. In certain embodiments, the target stream can be vaporized in a separate piece of equipment prior to being subjected to the process of the present invention. Preferably, the target stream is superheated to a desired temperature. In carrying out the process of the present invention in accordance with various embodiments, the flow of any process gases to the reactor, including any inert carrier gas, will desirably be initiated first. Once the system is at a temperature above the dew point of the target stream, the target stream comprising a first aldehyde concentration is provided to the reactor. The target stream, which is now mixed with any process gases, is contacted with catalyst at desired conditions, including temperature, pressure, and flow. As a result, aldehyde levels are reduced. A treated stream comprising a second aldehyde concentration, which is less than the first aldehyde concentration, is removed from the reactor.

The temperature and pressure that may be employed for the process is otherwise not generally limited. Depending upon other process conditions, the process can be conducted at a temperature as low as 150° C., as low as 125° C., as low as 100° C., and even as low as 50° C. Depending upon other process conditions, the process can be conducted at temperatures as high as 150° C., as high as 175° C., as high as 200° C., and even as high as 250° C. Preferably, the temperature should be chosen to control not only the reduction of aldehyde but also to avoid unselective oxidation reactions that increase with temperature. In certain embodiments, it will be desirable to keep the temperature under 225° C., more desirably under 200° C., to avoid decomposition of any carbonylatable reactants, including, but not limited to, methyl acetate and methanol, that may be present in the target stream.

The process is not generally limited by the pressure within the reactor. Conditions, including pressure, should be chosen such that the carbonylatable reactant or other non-aldehyde species which are desired to be preserved are not oxidized or otherwise decomposed to any significant extent. Depending upon other process conditions, in preferred embodiments, the process is generally conducted at pressures ranging from 0 to 150 psig. As will be appreciated by one of ordinary skill have the benefit of this disclosure, temperature, pressure, oxygen concentration (if an oxygen regime is being employed) and other factors will vary depending upon such issues as space velocity and desired conversion and will also vary based on the composition of the target stream, such as whether the stream comprises carbonylatable reactant as a major component. For example, one may vary temperature or oxygen concentration to maintain a desired level of conversion. Indeed, over the life of a catalyst, it can be expected that it will be desirable to operate over a range of temperatures. While it is appreciated that the selection of process conditions for the various embodiments of the present invention to achieve the desired result of reducing the aldehyde concentration of a target stream from a first aldehyde concentration to a second aldehyde concentration might be somewhat complex and time-consuming, such an effort would nevertheless be a routine undertaking for those of ordinary skill in the art having the benefit of this disclosure.

The step of subjecting the target stream to a reaction can be conducted in any number of vessels that are suited for maintaining conditions suitable for achieving the reduction in aldehyde concentration. Preferably, the vessel, or reactor, is capable of operating in a continuous mode such that a target stream with a first aldehyde concentration can be subjected to the process with a treated stream containing a second aldehyde concentration that is lower than the first aldehyde concentration being removed. It is contemplated that various reactor designs commonly used for heterogeneous catalysis can be used in conjunction with the various embodiments of the present invention. Thus, it is contemplated that gas phase, slurry phase, fixed bed, trickle bed, and fluidized bed reactors can be used in practicing the present invention. Gas phase, fixed bed reactors are preferred.

The process of the present invention reduces the concentration of aldehyde species from a first aldehyde concentration to a second aldehyde concentration. The desired reduction in amount of aldehyde concentration can be expected to be dependent upon certain factors that are unique to each implementation of the process. For example, in preferred embodiments where the process is employed to treat a feed stream of a carbonylation process, the desired reduction in amount of aldehyde concentration will generally be dictated by the product quality requirements of the acetic acid product of the carbonylation process. The process can be operated to achieve reductions in aldehyde concentration over a broad range. The reduction in aldehyde concentration from a first aldehyde concentration to a second aldehyde concentration can be conveniently measured as (first aldehyde concentration−second aldehyde concentration)/first aldehyde concentration×100%. Depending upon the process conditions and desired goals for each implementation, reduction in aldehyde concentration of as much as 25%, even as much as 50%, even as much as 75%, and as much as 99.9% can be achieved.

As disclosed, in certain embodiments, the target stream may also contain one or more carbonylatable reactants. Carbonylatable reactants are those species that can be reacted in a carbonylation process to produce acetic acid. Such carbonylatable reactants include, but are not limited to, methanol, methyl acetate, methyl formate, dimethyl ether, or mixtures thereof. Particularly desirable uses of the present invention are in the treatment of target streams comprising methyl acetate, methanol, or combinations of methyl acetate and methanol.

In embodiments in which the target stream also comprises carbonylatable reactant, this reduction in the concentration of aldehyde species is desirably achieved without a significant reduction in the concentration of carbonylatable reactant originally found in the target stream. That is, the concentration of carbonylatable reactant in a treated stream recovered as a result of practicing the process is not significantly reduced as compared to the concentration of carbonylatable reactant in the target stream.

In accordance with various embodiments of the present invention, the process is used to treat a target stream of a carbonylation process. Such target streams of a carbonylation process may or may not contain carbonylatable reactant, and if carbonylatable reactant is present, the concentration of carbonylatable reactant in the target stream may vary widely.

Target streams of a carbonylation process that can be subjected to the process of the present invention include process stream(s) within the carbonylation process and feed stream(s) provided to the carbonylation reactor.

Internal process streams, i.e., process streams, of a carbonylation process comprising at least one aldehyde species, and which may or may not additionally comprise carbonylatable reactant, that can be subjected to the process of the present invention include, but are not limited to a light ends column overhead, a light ends stripper column overhead, a drying column overhead, and/or other process streams.

A more desirable use of the present invention is in the treatment of a feed stream of a carbonylation process that contains at least one carbonylatable reactant and a first aldehyde concentration that is desired to be reduced before the feed stream is provided to a carbonylation reactor of a carbonylation process. Desirable feed streams that can be subjected to the process of the present invention comprise a carbonylatable reactant or a combination of carbonylatable reactants as a major component. Desirable feed streams comprise methyl acetate, methanol, or combinations of methyl acetate and methanol. Even more desirable feed streams comprise methyl acetate, methanol, or combinations of methyl acetate and methanol as a major component of the feed stream.

One of ordinary skill in the art having the benefit of this disclosure will appreciate that catalysts that can be used in practicing the present invention may, over time, deactivate due to circumstances that may be permanent, reversible, or partially reversible. Deactivation may occur when operating the process of the present invention under either oxidation or decomposition conditions. When deactivation is due either solely or partially to reversible or partially reversible mechanisms, it will be desirable to regenerate the catalyst. Regeneration may result in a full or partial recovery of catalyst activity. Regeneration is an aspect of the present invention.

In accordance with various embodiments of the present invention, regeneration can be achieved by several methods. One acceptable method is to subject the catalyst to oxidizing conditions, preferably in the absence of the target stream, and preferably at elevated temperatures. A certain level of regeneration may also be achieved by conducting the process of the present invention, i.e., in the presence of the target stream, under high oxygen concentrations, desirably greater than 1 mole % oxygen, more desirably greater than 2 mole % oxygen, and even more desirably greater than 3 mole % oxygen. Acceptable oxygen concentrations for regeneration will generally be dependent on process limitations and the bed temperature that can be achieved. A typical set of conditions for regeneration would include operation at 3 mole % oxygen and 150° C. Operating at higher oxygen concentrations may allow for regeneration of catalyst in a shorter period of time or at a lower temperature. In various embodiments, catalyst regeneration may be facilitated by using fluidized reactor beds in which a portion of the catalyst is constantly being refreshed or by employing multiple reactor beds, with the beds being regenerated when they are not being actively employed for the process.

As disclosed, a preferred embodiment of the present invention is the treating of a target stream of a carbonylation process comprising a first aldehyde concentration, which may or may not additionally comprise carbonylatable reactant. In such embodiments, the target stream comprising a first aldehyde concentration is provided to a reaction vessel containing a supported catalyst comprising at least one Group 8 to Group 11 metal. In the reaction vessel, the target stream is subjected to conditions sufficient to reduce the first aldehyde concentration. A treated stream comprising a second aldehyde concentration that is less than the first aldehyde concentration is removed from the reactor vessel. In embodiments where the target stream additionally comprises carbonylatable reactant, the treated stream will also comprise carbonylatable reactant.

As disclosed, in accordance with another preferred embodiment, the target stream is a feed stream of a carbonylation process. In such embodiments, a feed stream of a carbonylation process comprising a carbonylatable reactant and a first aldehyde concentration is provided to a reaction vessel containing a supported catalyst comprising at least one Group 8 to Group 11 metal. In the reaction vessel, the target stream is subjected to conditions sufficient to reduce the first aldehyde concentration. A treated stream comprising carbonylatable reactant and a second aldehyde concentration that is less than the first aldehyde concentration is removed from the reactor vessel and then provided either directly or indirectly, which may include being combined with other feedstocks, to a carbonylation reactor. In such embodiments, the treated stream is desirably condensed prior to being provided to the carbonylation reactor.

To facilitate a better understanding of the present invention, the following examples of certain aspects of some embodiments are given. In no way should the following examples be read to limit, or define, the scope of the invention.

EXAMPLES

Example 1

Experiments were conducted in a lab-scale gas-phase fixed bed plug flow tubular reactor. For each experiment, catalyst (8 cubic centimeters) was loaded into a 0.5 inch internal diameter×48 inch long stainless steel tube. Catalysts used included 0.5 wt. % Pd on granulated carbon (Catalyst A, 3.41 g, Engelhard Co., product no. C3880), 0.5 wt. % Pt on granulated carbon (Catalyst B, 3.32 g, Engelhard Co., product no. C3757) and 1.0 wt. % Ru on granulated carbon (Catalyst C, 5.5 g, Engelhard Co., product no. C4023). The temperature in the reactor was controlled by electrical heater. The top of the reactor was packed with quartz and served as pre-heater/mixer tube. Liquid feed containing aldehyde was pumped into the reactor at a flow of 0.75-1.1 cubic centimeters per minute and is vaporized in the top of the reactor tube. A 3 mole % $O_2$ in nitrogen carrier gas was fed at a rate of 305 standard cubic centimeters per minute (sccm) and added to the liquid feed before the reactor. The flow rates and reactor temperatures were selected in order to maintain the vapor phase mixture outside the explosive limits. Reactor effluent was cooled and condensed products were weighed and analyzed by offline GC. The non-condensable gaseous stream containing unreacted feeds and products was vented through a back pressure regulator. The reactor was run at 50 psig. The liquid feed contained 76 wt. % methyl acetate (MeOAc), 24 wt. % methanol (MeOH), around 840 ppm acetaldehyde (AcH), 104 ppm ethyl acetate, 18 ppm dimethylacetal and other trace components. Only minor amounts of impurities are found in the product including ppm levels of methyl formate, acetic acid, dimethyl carbonate and water. The results for three Runs, A, B, and C, are shown below. LHSV is liquid hour space velocity.

TABLE 1

| Run | LHSV ($h^{-1}$) | % Reduction in AcH concentration Temperature | | |
|---|---|---|---|---|
| | | 150° C. | 175° C. | 200° C. |
| A | 9.07 | 95.4 | 96.2 | 99.7 |
| B | 6.68 | 98.5 | 98.6 | 99.1 |
| C | 7.23 | 26.6 | 45.8 | 76.5 |

Example 2

Experiments were conducted as described for Example 1 except that nitrogen ($N_2$) was used as carrier gas. The results for three Runs, A, B, and C, are shown below.

TABLE 2

| Run | LHSV ($h^{-1}$) | % Reduction in AcH concentration Temperature | | |
|---|---|---|---|---|
| | | 150° C. | 175° C. | 200° C. |
| A | 9.07 | 62.4 | 84.0 | 97.1 |
| B | 7.14 | 20.2 | 51.1 | 80.3 |
| C | 7.47 | 38.2 | 43.8 | 54.6 |

Example 3

Experiments were conducted in a lab scale gas-phase fixed bed plug flow tubular reactor. For each experiment, catalyst (200 cubic centimeters, 0.5% Pd on carbon, Engelhard Co., product no. C3880) was loaded into a 1.6 inch internal diameter×60 inch long stainless steel tube. The temperature in the reactor was controlled by heat tapes and clam-shell heater. The top of the reactor was packed with quartz. Liquid feed containing acetaldehyde was pumped into a preheater/mixer tube packed with quartz at a flow of 6.2-15.1 cc/min. Carrier gas comprising nitrogen containing from 0 to 6 mole % $O_2$, as indicated in Table 3, was fed at a rate of 450-810 sccm. The flow rates and temperature of the preheater/mixer were selected in order to maintain the vapor phase mixture outside the explosive limits. The reactor was run at 50 psig and the liquid feed contained 76 wt. % methyl acetate (MeOAc), 24 wt. % methanol (MeOH), around 840 ppm acetaldehyde (AcH), 104 ppm ethyl acetate, 18 ppm dimethylacetal and other trace components. Reactor effluent was cooled and the condensed products were weighed and analyzed by offline GC. The non-condensable gaseous stream containing unreacted feeds and products was vented through a back pressure regulator. Off-line GCs of the non-condensable gas product stream verified that small amounts of CO, $CO_2$, and $CH_4$ were formed in the reaction. In the absence of oxygen, significant amounts of $CO_2$ were not formed. Only minor amounts of impurities were found in the product including ppm levels of methyl formate (MeFO), acetic acid (HOAc), water, and dimethyl carbonate. Results are shown below.

TABLE 3

| Run | Temp. (°C.) | mole % $O_2$ in gas | Gas Flow (sccm) | LHSV ($h^{-1}$) | % Reduction in AcH concentration | MeFO (ppm) | HOAc (ppm) |
|---|---|---|---|---|---|---|---|
| 1 | 152 | 3 | 810 | 5.0 | 77.6 | 386 | 60 |
| 2 | 173 | 3 | 810 | 4.9 | 86.9 | 128 | 130 |
| 3 | 202 | 3 | 810 | 5.0 | 98.3 | 13 | 283 |
| 4 | 146 | 6 | 810 | 4.8 | 92.9 | 1343 | 57 |
| 5 | 177 | 6 | 810 | 5.0 | 95.0 | 349 | 189 |
| 6 | 198 | 6 | 810 | 4.9 | 99.3 | 75 | 295 |
| 7 | 152 | 3 | 450 | 2.1 | 89.7 | 219 | 178 |
| 8 | 177 | 3 | 450 | 2.1 | 98.1 | 31 | 311 |
| 9 | 200 | 3 | 450 | 2.1 | 100.0 | 0 | 528 |
| 10 | 151 | 6 | 450 | 2.0 | 95.8 | 848 | 233 |
| 11 | 176 | 6 | 450 | 2.1 | 99.9 | 47 | 452 |
| 12 | 200 | 6 | 450 | 2.0 | 100.0 | 31 | 680 |
| 13 | 150 | 0 | 450 | 2.1 | 69.8 | 0 | 124 |
| 14 | 176 | 0 | 450 | 2.1 | 98.6 | 1 | 255 |
| 15 | 199 | 0 | 450 | 2.1 | 100.0 | 0 | 409 |

Therefore, the present invention is well-adapted to carry out the objects and attain the ends and advantages mentioned as well as those which are inherent therein. While the invention has been depicted and described by reference to exemplary embodiments of the invention, such a reference does not imply a limitation on the invention, and no such limitation is to be inferred. The invention is capable of considerable modification, alternation, and equivalents in form and function, as will occur to those ordinarily skilled in the pertinent arts and having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalents in all respects.

What is claimed is:

1. A process comprising: contacting a gas phase target stream that comprises a carbonylatable reactant and a first aldehyde concentration with a supported catalyst that comprises at least one Group 8 to Group 11 metal at conditions sufficient to reduce the first aldehyde concentration to a second aldehyde concentration.

2. The process of claim 1, wherein the carbonylatable reactant comprises at least one member selected from the group consisting of methanol, methyl acetate, methyl formate, and dimethyl ether.

3. The process of claim 1, wherein the target stream comprises a target stream of a carbonylation process.

4. The process of claim 3, wherein the target stream comprises a process stream of the carbonylation process.

5. The process of claim 3, wherein the target stream comprises a feed stream of the carbonylation process.

6. The process of claim 1, wherein the first aldehyde concentration comprises acetaldehyde.

7. The process of claim 1, wherein the support comprises carbon.

8. The process of claim 1, wherein the support comprise carbon from coconut.

9. The process of claim 1, wherein the metal comprises at least one Group 8 to Group 10 metal.

10. The process of claim 1, wherein the metal comprises at least one Group 10 metal.

11. The process of claim 1, wherein the metal comprises at least palladium.

12. The process of claim 1, wherein the metal comprises at least platinum.

13. The process of claim 1, wherein the conditions comprise an oxidation regime.

14. The process of claim 1, wherein the conditions comprise a decomposition regime.

15. The process of claim 1, wherein the conditions comprise a molar ratio of oxygen feed to first aldehyde concentration greater than 0.5.

16. The process of claim 1, wherein the conditions comprise a molar ratio of oxygen feed to first aldehyde concentration greater than 1.

17. The process of claim 1, further comprising regenerating the catalyst.

18. A process comprising: contacting a target stream of a carbonylation process comprising a first aldehyde concentration in the gas phase with a supported catalyst comprising at least one Group 8 to Group 11 metal within a reaction vessel at conditions sufficient to produce a treated stream having a second aldehyde concentration that is less than the first aldehyde concentration; and removing the treated stream from the reaction vessel.

19. The process of claim 18, wherein the carbonylatable reactant comprises at least one member selected from the group consisting of methanol, methyl acetate, methyl formate, and dimethyl ether.

20. The process of claim 18, wherein the target stream comprises a process stream of the carbonylation process.

21. The process of claim 18, wherein the target stream comprises a feed stream of the carbonylation process.

22. The process of claim 18, wherein the first aldehyde concentration comprises acetaldehyde.

23. The process of claim 18, wherein the support comprises carbon.

24. The process of claim 18, wherein the support comprise carbon from coconut.

25. The process of claim 18, wherein the metal comprises at least one Group 8 to Group 10 metal.

26. The process of claim 18, wherein the metal comprises at least one Group 10 metal.

27. The process of claim 18, wherein the metal comprises at least palladium.

28. The process of claim 18, wherein the metal comprises at least platinum.

29. The process of claim 18, wherein the conditions comprise an oxidation regime.

30. The process of claim 18, wherein the conditions comprise a decomposition regime.

31. The process of claim 18, wherein the conditions comprise a molar ratio of oxygen feed to first aldehyde concentration greater than 0.5.

32. The process of claim 18, wherein the conditions comprise a molar ratio of oxygen feed to first aldehyde concentration greater than 1.

33. The process of claim 18, further comprising regenerating the catalyst.

34. A process comprising: providing a gas phase feed stream of a carbonylation process comprising a carbonylatable reactant and a first aldehyde concentration to a reaction vessel containing a supported catalyst comprising at least one Group 8 to Group 11 metal; contacting the gas phase feed stream with the supported catalyst within the reaction vessel at conditions sufficient to produce a treated stream comprising a second aldehyde concentration that is less than the first aldehyde concentration; and removing the treated stream from the reaction vessel.

35. The process of claim 34, wherein the first aldehyde concentration comprises acetaldehyde.

36. The process of claim 34, wherein the support comprises carbon.

37. The process of claim 34, wherein the support comprise carbon from coconut.

38. The process of claim 34, wherein the metal comprises at least one Group 8 to Group 10 metal.

39. The process of claim 34, wherein the metal comprises at least one Group 10 metal.

40. The process of claim 34, wherein the metal comprises at least palladium.

41. The process of claim 34, wherein the metal comprises at least platinum.

42. The process of claim 34, wherein the conditions comprise an oxidation regime.

43. The process of claim 34, wherein the conditions comprise a decomposition regime.

44. The process of claim 34, wherein the conditions comprise a molar ratio of oxygen feed to first aldehyde concentration greater than 0.5.

45. The process of claim 34, wherein the conditions comprise a molar ratio of oxygen feed to first aldehyde concentration greater than 1.

46. The process of claim 34, further comprising regenerating the catalyst.

* * * * *